United States Patent
Greatrex et al.

(10) Patent No.: US 10,022,480 B2
(45) Date of Patent: Jul. 17, 2018

(54) VENTRICULAR ASSIST DEVICE AND METHOD OF CONTROLLING SAME

(71) Applicant: Reinheart GmbH, Bad Oeynhausen (DE)

(72) Inventors: Nicholas Greatrex, Brisbane (AU); Ulrich Steinseifer, Hauset (BE)

(73) Assignee: REINHEART GMBH, Guetersloh (DE)

( * ) Notice: Subject to any disclaimer, the term of this patent is extended or adjusted under 35 U.S.C. 154(b) by 0 days.

(21) Appl. No.: 14/429,303

(22) PCT Filed: Sep. 21, 2012

(86) PCT No.: PCT/EP2012/003958
§ 371 (c)(1),
(2) Date: Mar. 18, 2015

(87) PCT Pub. No.: WO2014/044287
PCT Pub. Date: Mar. 27, 2014

(65) Prior Publication Data
US 2015/0246166 A1    Sep. 3, 2015

(51) Int. Cl.
*A61M 1/10* (2006.01)
*A61M 1/12* (2006.01)

(52) U.S. Cl.
CPC ......... *A61M 1/1086* (2013.01); *A61M 1/101* (2013.01); *A61M 1/122* (2014.02); *A61M 2205/3303* (2013.01); *A61M 2205/3334* (2013.01); *A61M 2205/3344* (2013.01); *A61M 2205/3365* (2013.01); *A61M 2205/50* (2013.01); *A61M 2210/125* (2013.01); *A61M 2230/04* (2013.01)

(58) Field of Classification Search
CPC ...... A61M 1/101; A61M 1/122; A61M 1/125; A61M 1/1086
See application file for complete search history.

(56) References Cited

U.S. PATENT DOCUMENTS

| | | | |
|---|---|---|---|
| 2010/0160801 A1 | 6/2010 | Takatani | |
| 2010/0222632 A1* | 9/2010 | Poirier | A61M 1/1086 600/16 |
| 2011/0160519 A1 | 5/2011 | Arndt | |
| 2012/0078030 A1* | 3/2012 | Bourque | A61M 1/1086 600/16 |

\* cited by examiner

*Primary Examiner* — Michael D Abreu
(74) *Attorney, Agent, or Firm* — Andrew Wilford

(57) ABSTRACT

The invention relates to a method of controlling the speed of a ventricular assist device, in particular the rotational speed of a rotary blood pump, wherein at least temporarily the speed of the device is modulated around a mean speed and a response of the native heart to this modulation is measured to determine the ventricular function/contractile state of the heart, in particular to determine whether the aortic valve opens and closes at the instant mean speed, and the mean speed is set, in particular a new mean speed is set in dependence of the measured response. The invention furthermore relates to a device performing the method.

7 Claims, 3 Drawing Sheets

VENTRICULAR ASSIST DEVICE AND METHOD OF CONTROLLING SAME

CROSS REFERENCE TO RELATED APPLICATIONS

This application is the US-national stage of PCT application PCT/EP2012/003958 filed 21 Sep. 2012 and claiming the priority of PCT patent application PCT/EP2012/003958 itself filed 21 Sep. 2012.

FIELD OF THE INVENTION

The invention relates to a vehicular assist device and to a method of controlling the speed of such a device.

BACKGROUND OF THE INVENTION

Due to improvements in their durability and performance Ventricular Assist Devices (VADs) have increasingly been used as a treatment of heart disease. In the past VADs traditionally featured displacement pumps which provided pulsatile support to the failing heart. Recently, rotary blood pumps have been used in VADs, due to the smaller size, higher efficiency and durability when compared with pulsatile pumps. Current commercially available VADs utilize both centrifugal and axial flow type rotary pumps to provide augmented perfusion to the circulatory. One of the lingering challenges with rotary VADs is their interaction with the circulatory system and native heart. Operation of the rotary VAD at a low speed could cause underperfusion of the circulatory system or regurgitate flow through the VAD and conversely an excessively high speed could cause a collapse of vessels in the inflow path potentially resulting in a suction event. Accordingly a correct operation of the device is mandatory and will improve patient quality of life and outcomes.

Rotary VADs are typically set at a constant operational speed by a clinician or trained operator. A change to the patient condition, either can alter the interaction between the device and the circulatory system. In the case of a change in patient condition, the previously set rotation speed of the VAD may no longer provide the desired level of cardiac support. Monitoring patients with these devices and their physiological changes is a difficult task. There are many methods of patient evaluation, such as echocardiaography, catheter based pressure and volume measurements as well as intrinsic feedback from the device itself. However most of these methods require a skilled practitioner to perform the evaluation or are invasive.

A noninvasive physiological monitoring and control system for a rotary blood pump would provide an indication of the patient condition for a particular VAD speed and determine a speed range to operate the device to not to only prevent undesirable events, but also to provide an improved level of support for the patient to promote recovery.

According to the well known state of the art currently the most common form of rotary blood pump control is fixed speed operation. A trained clinician or technician sets a target speed for the device to operate at and the device will attempt to operate at or close to this set speed value.

One method for determining an appropriate VAD speed is to find the VAD speed such that the Aortic valve is closed throughout the cardiac cycle. The speed at which the Aortic valve closes throughout the cardiac cycle is called the Aortic Valve Closure Speed (AVCS). Determining the AVCS can be determined using echocardiography imaging while the pump speed is increased. The AVCS is dependent on the heart's contractility level, preload, afterload and importantly the support of VAD. Accordingly it may change over time. The status of the Aortic valve is a critical piece of information for clinicians when assessing the condition of a patient with a VAD.

In the case of a VAD operating under constant speed control, any change, either short term or long term, to the patient physiological state will not elicit a change in the VAD's operational speed. To improve on the method of fixed speed control, feedback from the physiological system or device has been used to indicate both changes to the physiological system and a potentially appropriate VAD operation point.

Many of physiological feedback techniques utilize sensorless, or intrinsic measurements derived from the device's motor signals. Methods of estimating the pump head pressure, pump flow, heart beat and the pulsatility of the native heart from signals from the device have been proposed by a number of authors and have been implemented in commercially available pumps, for example according to U.S. Pat. No. 7,887,479, US Patent Application 20110054239. This feedback information is typically displayed to the clinical staff to assist in their diagnosis of the pump state.

Other feedback mechanisms that utilize intrinsic measurements seek to determine the status of the native heart through the analysis of pump signals. One such method is the pulsatility index which is a measure of the pulsatility of the native heart when operating with a VAD. The pulsatility of a signal such as motor power or current can give an indication of the pulsatility of the ventricle, and therefore the assistance of the device.

Pressure sensors placed at the inlet or outlet of the VAD or cannulas have been suggested to determine the afterload, preload or pressure difference over the device, however the long term accuracy and stability of pressure sensors has restricted this technique's implementation in long term implantable devices. Sensor based feedback based on a flow sensor placed on the outlet cannula, has been included on a commercially available device.

Due to the difficulties in regularly monitoring and assessing changes to the circulatory hemodynamics the speed of the VAD is typically set by the clinician or trained expert and remains fixed until the next evaluation is performed by the specialist.

A monitoring system that could evaluate the patient's physiological status, such as if the Aortic valve is closed, would be invaluable to the specialists to determine if the VAD speed needs to be reviewed.

In cases when patient recovery is expected, the status of the Aortic valve is critical for evaluating the recovery. Weaning a patient off a VAD is a very difficult procedure where the native heart function must be evaluated to determine if the VAD could be removed from the patient. One of the best indications of the patient's left ventricle contractile state is the AVCS. An increase of contractility (patient native heart improvement) will see an increase in the AVCS while a decrease in contractility will see the AVCS fall.

Many authors have described the risk of consistently operating a VAD at a speed at which the Aortic valve does not open during the cardiac cycle. Long-term operation in this condition can lead to fusion of the leaflets and degrading the functionality of the valve. As such it is important to be able to periodically ensure that the pump operates, even if only temporarily, at a speed at which the valve leaflets open. The most robust method for determining the status of the Aortic valve is to use Echocardiography, which must be performed by a trained technician or clinician and as such is often only performed when required or scheduled. As such, due to the difficulties in assessing the operation of the aortic valve, any changes to the AVCS is not monitored regularly.

Currently many of the controllers and feedback measurements are based around sensorless or intrinsic measurements. Although these sensorless methods can provide some indication of the current status of the pump, however they fail to give adequate information regarding the physiological state of the heart or circulatory system. Many of these measurements of pump performance inferred from motor or device status can be susceptible to parameter variations including blood viscosity, blood clots and temperature.

Other derived measurements such as pulsatility index can be susceptible to short term changes in contractility or preload making them inappropriate for tight physiological monitoring. Sensor based feedback can provide more direct estimation of the pump operation, however drift of the sensors over their long implantable lifetime has made their clinical use limited.

OBJECT OF THE INVENTION

It is an object of the invention to provide a method of operating a ventricular assist device, in particular a rotary blood pump, at a specific speed or with a specific speed profit assuring that the aortic valve opens during contractions of the assisted heart.

The proposed invention seeks to operate the pump of the VAD with a defined speed profile different from constant speed at least at certain times and the response of the patient hemodynamics is measured and used to estimate the status of the ventricle, in particular left ventricle and circulatory system.

SUMMARY OF THE INVENTION

According to the invention this object is solved by the features that the speed, in particular rotational speed of the VAD is modulated, in particular at a low frequency and low amplitude, meaning that the rotational speed is changed within a certain time between two different speed values, in particular two different speed values surrounding the instant mean speed of the VAD and that the response of the native heart to these speed changes is determined. In dependence of the result of the measured response or the measured value(s) representing the response the instant mean speed of the VAD may be changed to a new mean speed value, in particular a new mean speed value having a certain difference to the AVCS, in particular being lower than the AVCS by a certain difference.

This method of pump perturbation and measurement can be used as a monitoring tool to provide feedback to clinical staff or preferably as part of an automatic feedback controller that changes the mean VAD rotational speed in response to a change in patent condition. In particular by this method of operating the VAD it is possible to determine if the aortic valve remains closed throughout the cardiac cycle or if the natural ventricle is ejecting through the valve in systole. The latter is the preferred method of operating the VAD.

BRIEF DESCRIPTION OF THE DRAWING

A possible embodiment is shown in the figures and described in more detail. Even though the following features are described in connection with a specific embodiment the mentioned features are not restricted to this embodiment and are generally applicable to all possible VAD's. In the drawing.

SPECIFIC DESCRIPTION OF THE INVENTION

Pump Connection

Figure 1:
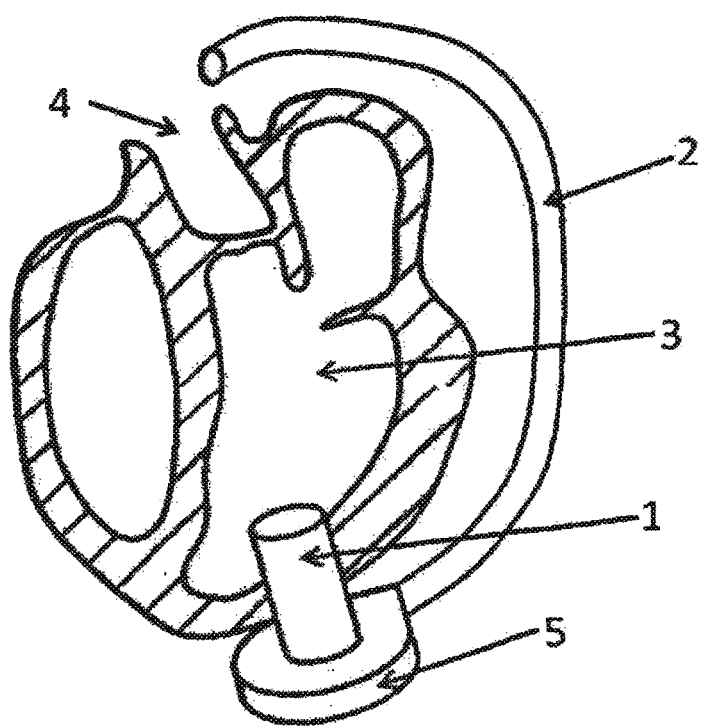
FIG. 1 is a largely schematic view of the invention in a heart.

In a possible embodiment the methodology can be applied to VAD that may be a rotary blood pump which is installed in a bypass configuration as shown in FIG. 1. The inlet of the device (1) should be connected directly or via a cannula to the left ventricle (2). The outlet of the device should be connected directly or via a cannula (3) to the Aorta (4). The rotary blood pump (5) can be any type of heart assist device including axial, diagonal, centrifugal or radial pumps which are implanted or positioned extracorporeally.

Speed Modulated Pump Operation for Monitoring

Figure 2:
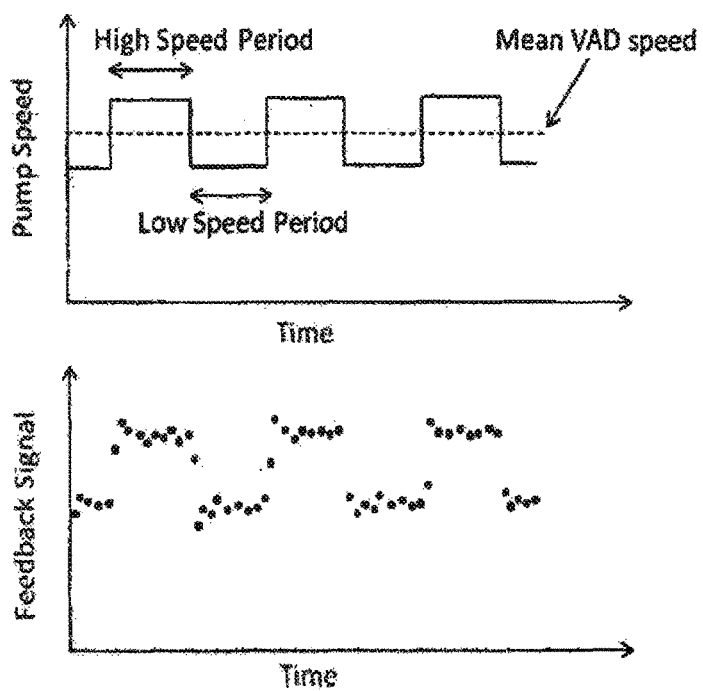
FIG. 2 is a graph illustrating operation of the invention.

Without restriction to this embodiment to determine the condition of the patient, a speed change, in particular a periodic speed change is applied to the pump as shown in FIG. 2 (top). The pump speed will be accelerated to a higher speed (higher than instant mean speed) and left for a period of time (High Speed Period). The pump will then be decelerated to a lower speed (lower than instant mean speed) and left for a period of time (Low Speed Period) and observed.

A feedback signal will be measured and the response of this feedback signal at the lower and higher pump rotational speeds will then be used to determine the status of the patient and in particular their left ventricular function.

This speed change, in particular periodic speed change, also referred to as speed modulation, may be engaged during a specific time of operating the VAD when the status of the patient shall be determined, accordingly it is not necessary to always be enabled, in particular when only periodical measurements of the patient status are performed. Accordingly there may exist times of operating the VAD at constant speed and times of operating the pump to determine the status of the patient by speed modulation.

The speed modulation should be significant enough to illicit a measurable response from the entire system comprising the VAD and the blood circuit, however small enough so that the overall performance of the pump is not significantly changed from constant speed operation.

The frequency of the speed modulation should be low enough to observe a change in the physiological system. This would typically mean a frequency which is low enough that multiple heart beats (at least two) occur within a single high speed and low speed period. The frequency of the speed modulation can be chosen by a clinician or trained expert, however the monitor or controller can automatically increase or decrease the speed modulation frequency.

The amplitude of the speed modulation should be chosen such that there is an observable change to the feedback variable. The amplitude of the speed modulation can be chosen by a clinician or trained expert, however the monitor or controller can automatically increase or decrease the amplitude.

Feedback Signal

To assess the contractile state of the ventricle one or more feedback signals (FS) need to be measured. The measured feedback signal is the value of an appropriate feedback variable. A wide range of feedback variables can be used in conjunction with the speed modulated VAD, in particular rotary pump. One or more specific sensors may be used to measure the value of such a feedback variable.

Figure 3:
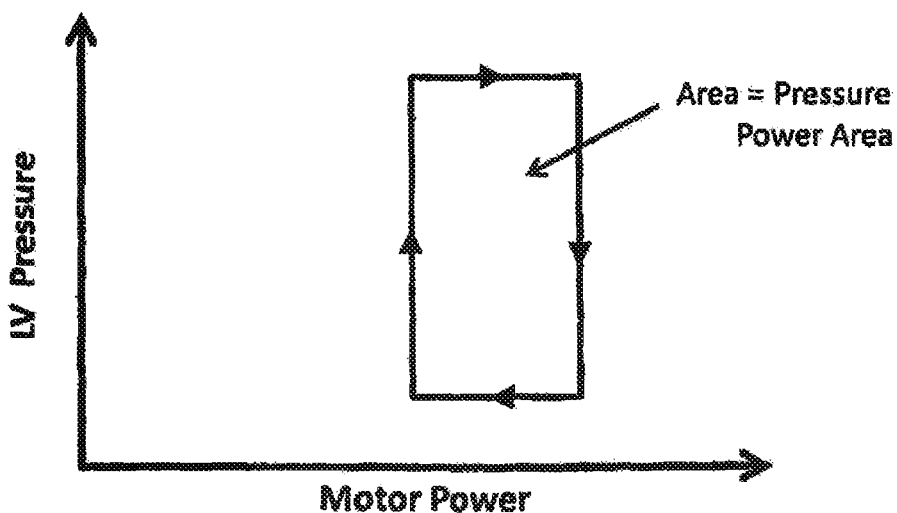
FIG. 3 and 4 are further graphs illustrating the invention.

A feedback variable should be chosen such that its value
Exhibits a significant value change in response to a change of patient or pump conditions.
Before the Aortic valve closure speed, the value is flat or monotonically increases with a increase of pump speed.
After the Aortic valve closure speed, the value monotonically decreases until suction or occlusion occurs at the higher speeds.
Without loss of generality some appropriate Feedback Variables are
Pulsatility index (PI) determined from the LV pressure, flow sensor or pump parameter (such as motor power or current)
Ventricle volume (end diastolic volume), particularly as measured by a catheter or echocardiography measurement
End diastolic pressure, particularly as determined by a pressure sensor inserted in the LV or attached to the inlet of the VAD
Stroke Volume, particularly as determined by a left ventricle volume catheter
External work of the ventricle, particularly as determined by a pressure volume catheter placed in the LV.
A combination of intrinsic and extrinsic variables. In particular the area of the LV pressure and the motor power (Pressure Power Area or PPA) in a single heart beat (FIG. 3).
Measurement and Control Algorithm To determine the contractile state of the patient the change of feedback signal must be determined for the known change in the pump speed.

When the mean VAD speed is lower than the AVCS an increase in speed will result in an increase or no change to the feedback signal. When the mean VAD speed is higher than the AVCS an increase in speed will result in a decrease to the feedback signal.

As such if the feedback signal during the high speed period is higher or equal to the low speed period then the pump is operating below the AVCS. If the feedback signal during the high speed period is lower than the low speed period then the pump is operating higher than the AVCS.

The comparison between the high and low speed time periods is determined by a difference or gradient between the values, in particular average values of the feedback signal during each time period.

Figure 4:
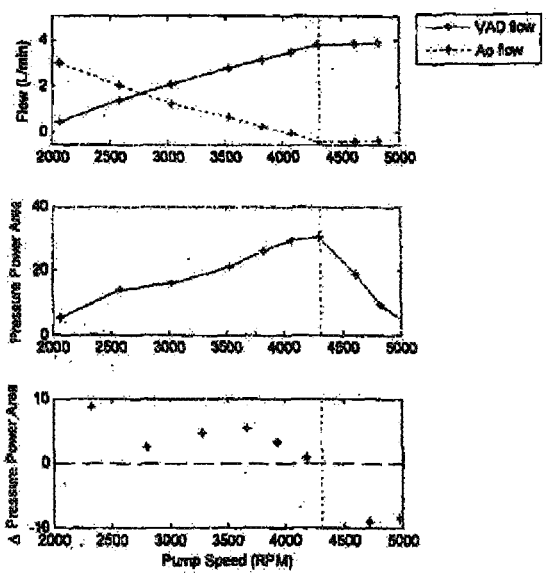

An example of this system is shown in FIG. 4. FIG. 4 top shows the mean flow through the Aortic valve and through the VAD at various pump speeds. At 4300 rpm the mean aortic flow becomes zero indicating the Aortic valve is closed. FIG. 4 (middle) shows the response of the feedback signal (in this case the PPA) in response to the VAD operating at a constant speed.

As expected the value of the PPA increases in response to an increase in VAD speed before the AVCS and decreases in response to an increase in VAD speed after the AVCS. FIG. 4 bottom shows the difference between the PPA signal at a higher speed and a lower speed. The differences are positive until the AVCS when they become negative.

Figure 5:
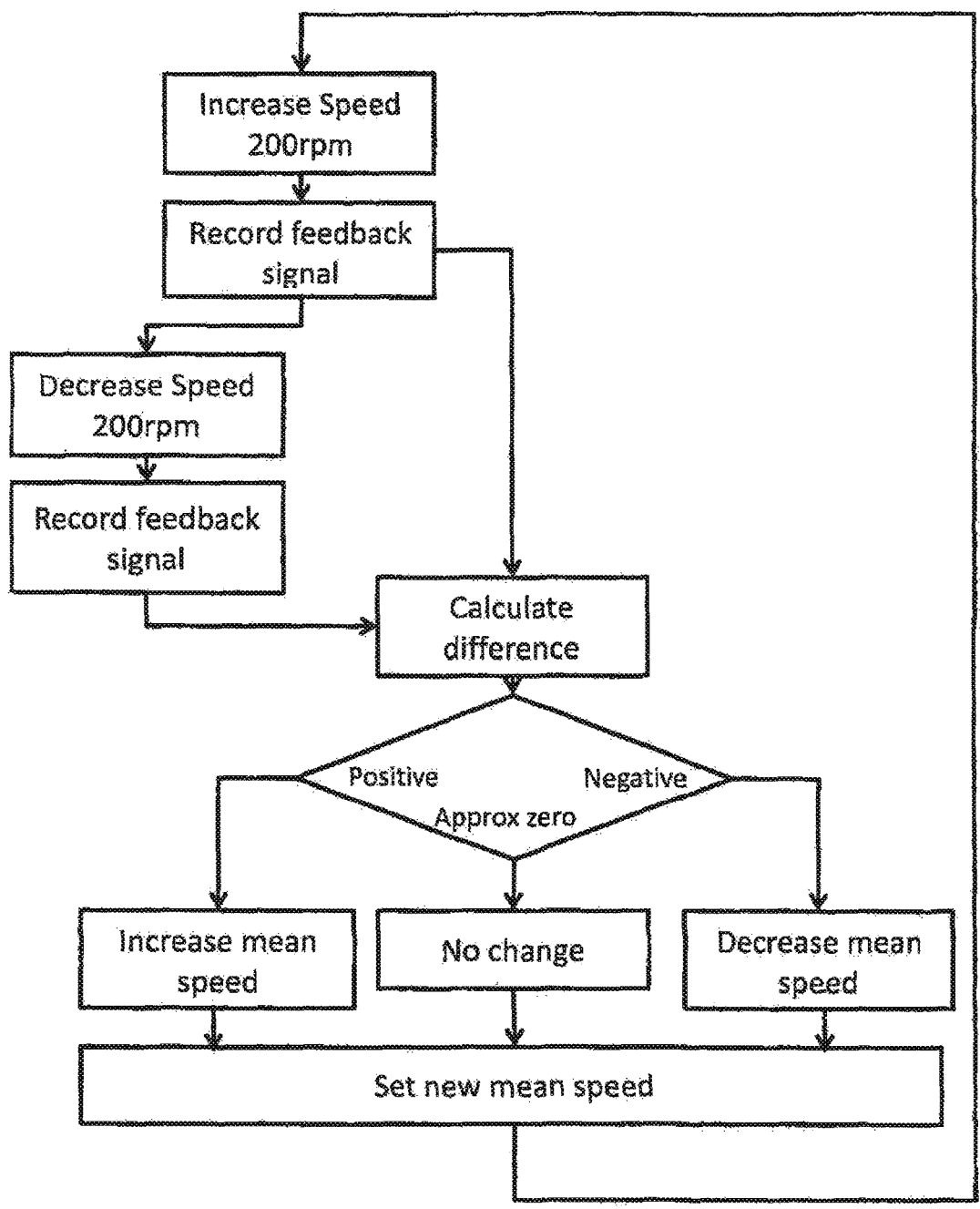
FIG. 5 is a block diagram illustrating the invention.

An automatic controller can be used to change the mean VAD speed such that the VAD operates close to the AVCS, preferably lower than the AVCS by a certain amount FIG. 5 demonstrates an automatic control algorithm. Originating from the instant mean rotational speed of the VAD the speed is increased by a certain amount (by 200 RPM in this example) and the feedback signal is recorded. The pump speed is then decreased by a certain amount (by 200 RPM in this example with respect to the instant mean rotational speed) and the feedback signal is again recorded. The feedback signal at the low speed period is subtracted from the high speed period to determine the difference (or gradient). If the difference is positive then the pump is operating below the AVCS and the mean pump speed should be increased. If the difference is negative then the pump is operating below the AVCS and the mean pump speed should be decreased. If the difference is zero (or close to zero) then the mean pump speed can remain the same.

Preferably an increase or decrease of the mean pump speed does not exceed the value of the amplitude used during modulating the speed (in this example 200 RPM).

Suction or occlusion of the inlet cannula during the measurement should be avoided. Additional detection of these adverse events should be included when using the automatic controller in order to reduce the chance of an incorrect reading.

SUMMARY

Modulation of the pump rotational speed is used to make a defined change to the VAD and the circulatory system. The change in feedback signal due to the change in pump speed can indicate the state of the circulatory system.
A positive change in the feedback signal due to a positive change in the VAD speed indicates the aortic valve is opening during the cardiac cycle.
A negative change in the feedback signal due to a positive change in the VAD speed indicates the aortic valve is closed throughout the cardiac cycle.
The absolute value of the feedback signals is not necessary, only the change of the signal between the high and low VAD speeds. As such offset drift of the pressure signal over time will not reduce the effectiveness of the technique.
The speed modulation method and measurement can be applied to different rotary blood pump designs, including axial flow, diagonal flow and radial flow pumps which are connected in bypass (between the LV and the aorta).

The invention claimed is:
1. A method of controlling speed of a ventricular assist device comprising, the steps of:
in a normal mode of operation driving a motor at a predetermined normal and constant speed, and, periodically during an evaluation mode of operation:
modulating the predetermined normal speed by
for a period of at least two successive heart beats increasing the speed of the device to a speed higher than the predetermined normal speed,
maintaining the higher speed for a first certain time,
measuring values of a combination of intrinsic and extrinsic variables as a high-speed feedback signal representing the response of the heart to this increase during a first certain time of a single heart beat,
for a period of at least two successive heart beats decreasing the higher speed of the device to a speed lower than the predetermined normal speed, and
maintaining the lower speed for a second certain time, measuring the values of a combination of intrinsic and extrinsic variables as a low-speed feedback signal representing the response of the heart to this speed decrease during the second certain time, when device is operating below an aortic valve closure speed, if the high-speed feedback signal is higher than or equal to the low-speed feedback signal, and if the device is operating above the aortic valve closure speed if the high-speed feedback signal is lower than the low-speed feedback signal;

evaluating the measured values to determine whether the aortic valve opens and closes at the predetermined normal speed by calculating the differences or gradient between the measured values at the predetermined normal speed, and resetting the predetermined normal speed depending on the result of the evaluation by increasing the predetermined normal speed if the sign of the difference or gradient is positive and decreasing the predetermined normal speed if the sign of the difference or gradient is negative so as to maintain the predetermined normal speed below the aortic valve closure speed by a certain amount and within a speed interval in which the sign of the difference or gradient changes.

2. A rotary blood pump comprising a controller configured to perform the method of claim 1.

3. The device according to claim 2, further comprising:
at least one sensor connected to the controller and capable of measuring directly values of a feedback variable or capable of measuring values for calculating a value of a feedback variable representing the ventricular function or contractile state of the heart.

4. The method according to claim 1, wherein modulation in done in the range of 1 to 10% of the instant predetermined normal speed.

5. The method according to claim 1, wherein a change of the predetermined normal speed after evaluating the hearts response to the speed modulation is less than the modulation amplitude.

6. The method defined in claim 1, wherein the intrinsic variable is a power of the motor driving the device and the extrinsic variable is a of pressure in the left ventricle.

7. The method defined in claim 1, wherein the combination of extrinsic and intrinsic variables is an area of a space defined between curves of the extrinsic and intrinsic variables plotted against each other.

* * * * *